(12) United States Patent
Fischell et al.

(10) Patent No.: US 10,589,117 B1
(45) Date of Patent: Mar. 17, 2020

(54) INTEGRATED MAGNETIC PULSATION DEVICE FOR THE TREATMENT OF FOOT PAIN

(71) Applicant: ZYGOOD, LLC, Dayton, MD (US)

(72) Inventors: Robert E. Fischell, Dayton, MD (US); Stephen T. Kaye, Ellicott City, MD (US)

(73) Assignee: Zygood, LLC, Dayton, MD (US)

(*) Notice: Subject to any disclaimer, the term of this patent is extended or adjusted under 35 U.S.C. 154(b) by 0 days.

(21) Appl. No.: 16/232,315

(22) Filed: Dec. 26, 2018

(51) Int. Cl.
*A61N 2/00* (2006.01)
*A61N 2/02* (2006.01)
*A61N 2/04* (2006.01)

(52) U.S. Cl.
CPC .............. *A61N 2/008* (2013.01); *A61N 2/02* (2013.01)

(58) Field of Classification Search
CPC ........ A61N 2/004; A61N 2/006; A61N 2/008; A61N 2/002; A61N 2/12
See application file for complete search history.

(56) References Cited

U.S. PATENT DOCUMENTS

2010/0160712 A1* 6/2010 Burnett .............. A61N 1/36007 600/13
2015/0360045 A1* 12/2015 Fischell .................. A61N 2/02 600/14

* cited by examiner

*Primary Examiner* — Christine H Matthews
*Assistant Examiner* — Joshua Daryl D Lannu
(74) *Attorney, Agent, or Firm* — Rosenberg, Klein & Lee

(57) ABSTRACT

An integrated magnetic pulsation device for the treatment of foot pain that utilizes an electrical pulse generator and a magnetic coil situated within the same enclosure. The device having the capability to have a patient's foot placed onto the top of a magnetic coil or under that magnetic coil to expose that patient's foot to a series of high intensity magnetic pulsations. The device also including a control panel that directs a patient as to how to utilize the device for the treatment of that patient's foot pain.

19 Claims, 5 Drawing Sheets

INTEGRATED MAGNETIC PULSATION DEVICE FOR THE TREATMENT OF FOOT PAIN

FIELD OF USE

This invention is a device to be used by human subjects to decrease or eliminate foot pain or both foot and ankle pain by the application of a series of magnetic pulsations that are applied from a device that is designed to be placed on the floor.

INCORPORATION BY REFERENCE

U.S. Pat. Nos. 9,550,067 and 9,849,302 are hereby incorporated by reference.

BACKGROUND OF THE INVENTION

It is well known that there are literally tens of millions of patients throughout the world who suffer foot pain caused by cancer chemotherapy, plantar fasciitis or diabetic neuropathy. One serious side effect of such pain is that these patients do not have a normal walk, i. e., their gait is abnormal and not comfortable. Although there are many pain medications to reduce the level of pain experienced by such patients, these drugs often are not sufficiently palliative, and they typically can cause serious side effects.

One early invention to utilize magnetic fields to treat pain is described by Robert R. Holcomb in International Publication Number: WO 91/15263. The invention described in that document consists of four magnetic coils that are placed in the back of a chair or under a table where the patient's back would be exposed to the magnetic field. A DC current is placed through the four coils which results in an unchanging magnetic field to be experienced by the patient. Such a treatment with an unchanging magnetic field could have no therapeutic effect for any patient who would try to use such a treatment and is certainly not applicable for the treatment of foot pain.

In U.S. Pat. No. 6,402,678, Robert E. Fischell, et al describe a device to be placed on the head which can eliminate or reduce the pain of migraine headaches by the application of a series of intense magnetic pulses. This device was approved by the US FDA on May 22, 2014 and is currently in use to treat patients with migraine headaches. The Fischell, et al migraine treatment device operates by charging capacitors to a high voltage and then discharging them into a magnetic coil to create a magnetic pulse that reaches a peak intensity of about 0.8 Tesla in less than 200 microseconds. By Faraday's law, this changing magnetic field intensity creates an electrical pulse within the skull that has been shown to eliminate migraine headaches. Because it takes about 45 seconds to charge the condensers from a battery within this Transcranial Magnetic Stimulation (TMS) device, the rate of applying magnetic pulses to the brain is extremely slow; i. e., typically about one pulse per minute. Even at that, the time rate of change of the magnetic field within the brain and the neurons surrounding the brain results in an electrical current pulse in some neurons which can eliminate most migraine headaches. However, the application of more pulses per unit time and at a higher magnetic field intensity with a specially shaped magnetic coil does result in a more effective treatment for the relief of pain for other parts of the human body such as the feet for patients who suffer from foot pain caused by diabetic neuropathy or cancer chemotherapy.

An existing system that is currently available to treat lower back pain is called TENS which is an acronym for Transcutaneous Electrical Nerve Stimulator. This device has two adhesive covered electrodes that are pasted onto the patient's skin along the lower back or at several other possible locations. The device can then be turned on and the electrical intensity adjusted so that the pain in the skin is acceptable while some electrical pulses enter the body in the vicinity of the spine where they can provide some relief for lower back pain. However, it would be highly advantageous to use a system that could provide higher intensity electrical pulses much deeper into the body without causing any skin pain. That can be accomplished with TransCutaneous Magnetic Stimulation or TCMS as described herein.

One issued patent and three patent applications by Donald Burnett et al namely U.S. Pat. No. 6,701,185 (the '185 patent), and the patent publications US2003/0158585 (the '585 publication), US2004/0210254 (the '254 publication) and US2012/0302821 (the '821 publication). These inventions described in the Burnett et al patent and publications all have a consistent design for the use of magnetic pulsations for the treatment of pain, namely, comparatively small wire coils with all wires being in circular form and placed against the skin of the foot or wrapped around the knee or elbow with the use of comparatively low electrical currents. Specifically, this prior art has the following numbers of generally circular or curved magnetic coils: the '185 reference 6 coils; the '585 reference, 10 coils; the '254 reference, 9 coils; and the '821 reference, 30 coils. Not even one of these 49 coil designs has considered a single wire coil for the treatment of human pain. The Burnett et al references describe 23 different coil designs placed against the side of the foot and three different designs that are needles placed against the side of the foot. At no point in any of these prior art documents is there a single flat coil to be placed under the foot or on top of the foot for the treatment of foot pain.

In U.S. Pat. No. 9,550,067 (the '067 patent) and U.S. Pat. No. 9,849,302 (the '302 patent), Susan Fischell, et al describe in detail several types of foot coils for the treatment of foot pain. The '067 patent utilizes a single coil that is in the shape of a shoe. That design has several technical difficulties, namely: one size does not fit all foot pain patients. Therefore, many different sizes of magnetic coils would have to be made available for patients who have different sizes of their feet. It is also difficult for some patients to place his or her entire foot within this rigid structure of the foot-shaped magnetic coil and it takes more power to energize this coil shape because of its large size. The '302 patent utilizes three separate coils to cover the different regions of the foot. Each of the three coils is powered separately from a pulse generator and is used sequentially for the treatment of foot pain. An improved system as described herein would be able to use a single coil connected directly to a high current pulse generator to provide a sequential treatment for all surfaces of the foot and ankle from this single coil to eliminate or reduce foot pain.

SUMMARY OF THE INVENTION

The present invention is an Integrated Magnetic Pulser (IMP) device that is particularly advantageous for those patients who suffer foot and ankle pain resulting from extensive cancer chemotherapy or from diabetic neuropathy or the pain experienced at the bottom region of the foot which is called plantalgia that is caused by tissue inflammation at the bottom of the foot, which inflammation is also called plantar fasciitis.

The IMP system consists of a single magnetic coil that is situated within the same enclosure that includes an electrical pulse generator. The electrical pulse generator creates the intense electrical pulses that the magnetic coil converts into intense magnetic pulses. Within the human body, these magnetic pulses convert back to electrical pulses that cause the pain neurons to be unable to send the correct message to the brain which is the message that the brain recognizes as being pain. Since the electrical pulse generator and the magnetic coil are each placed within the same enclosure, there is no need to have a long, multi-strand, electrical wire with connectors at each end as was described by S. Fischell et al in U.S. Pat. No. 9,849,302. The electrical pulse generator would typically get its power by being plugged into a wall electrical socket. Although it is expected to have a wire to plug the IMP device into an electrical socket, the use of a primary or rechargeable battery for this device is certainly possible.

Unlike the pulse generator of the '302 patent cited herein that would be placed on a table with a multi-conductor wire connecting it to the magnetic coil placed on the floor, the entire IMP device is placed on the floor so that it is most convenient for a patient to use when sitting on a chair with the IMP device placed in front of that chair.

The main object of the present invention is to provide a simple, floor-mounted device for those patients who suffer from foot pain with the treatment of their foot and/or foot and ankle pain by the application of a series of at least three high intensity magnetic pulsations created by the IMP device.

Another object of this invention is to utilize a single, flat magnetic coil that is formed integral within the same enclosure as the electrical pulse generator that produces the high electric current pulses that are converted by the single magnetic coil into high intensity magnetic pulsations.

Still another object of this invention is to diminish the pain caused by diabetic neuropathy in the foot and/or foot and ankle.

Still another object of this invention is to diminish the pain caused by cancer chemotherapy in the foot and/or foot and ankle.

Still another object of this invention is to diminish the pain within the tissue at the bottom of the foot, which pain is called plantalgia.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
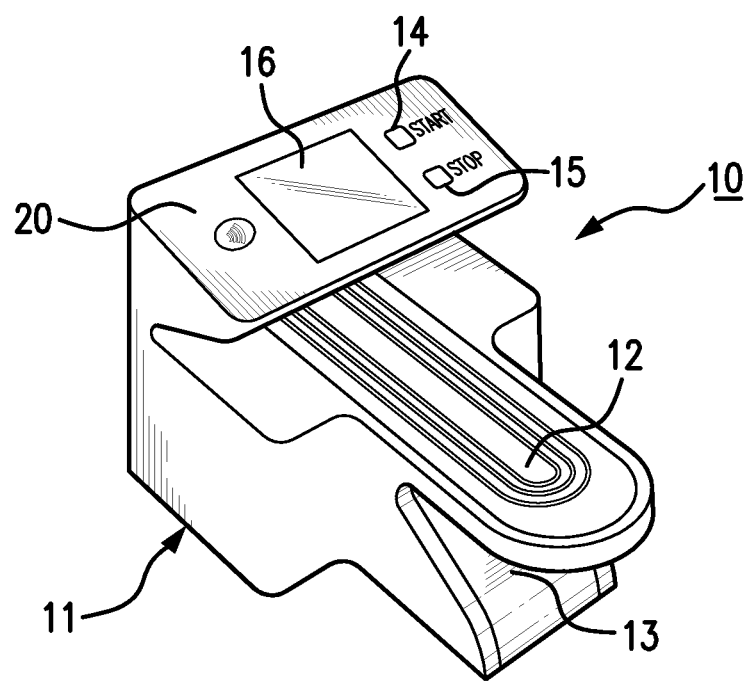
FIG. 1 illustrates the IMP device that includes an electrical pulse generator connected directly to a magnetic coil that is placed within the same enclosure, the system being designed for the treatment of foot pain.

FIG. 1 illustrates an angled view of the Integrated Magnetic Pulser (the IMP) system 10 that can be used for the treatment of foot pain or foot and ankle pain for essentially any human subject who suffers from that affliction. For its source of electrical power, the IMP device 10 has a means (not shown) to connect it to a conventional electrical outlet which in the USA would be for 115 Volts at 60 HZ. The IMP has only a single magnetic coil 12, but its design allows it to be used to treat all regions of the foot and the lower ankle. This is a considerable improvement over the shoe-shaped design of Fischell's '067 patent because the IMP is capable of treating a patient with any size of that patient's foot which is unlike a shoe-shaped coil of the '067 patent that requires a different size of the magnetic coil depending upon the size of that patient's foot. Also, the IMP design is superior to the design shown in the Fischell's '302 patent because only one coil instead of three coils is needed and there is no need for multiple external connecting wires and no need for any electrical sockets and plugs to join the pulse generator to the magnetic coil. That is, there are two short wires within the IMP device 10 enclosure that join the magnetic pulsing wire coil 12 to the pulse generator circuitry situated within the IMP device 10.

In FIG. 1 the IMP device 10 is shown to have an outer case 11, a magnetic coil 12 and an under-coil-opening 13. The case 11 could be formed as either a plastic or a metal shell. The magnetic coil 12 would typically have between 6 and 20 turns of an electrically conducting wire that would typically be made from copper. An optimum design for such a wire is rectangular in shape with the wire having a multiplicity of strands so that it has considerable flexibility for being readily wound into its racetrack shape. The under-coil-opening 13 is the site for the placement of the front of the patient's foot so that the top of his/her foot can be exposed to a series of high intensity magnetic pulses to decrease that patient's foot pain.

On the top of the IMP device 10 is the control panel 20 that has a START button 14, a STOP button 15 and a display panel 16. The entire operation of the control panel 20 will be described in greater detail with the description of FIG. 5 below.

Figure 2:
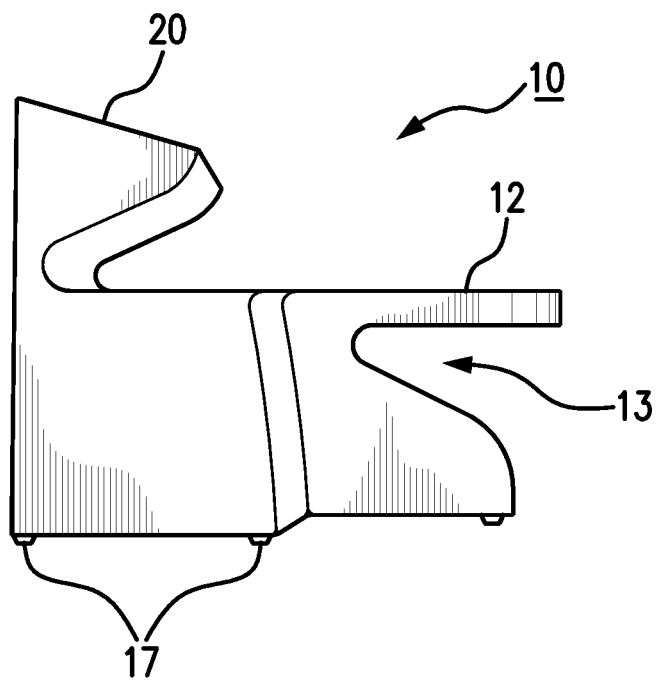
FIG. 2 is a side view of the IMP device for the treatment of foot pain.

FIG. 2 is a side view of the IMP device 10 showing the wire coil 12, the under-coil-opening 13, and the control panel 20. To prevent the IMP device 10 from sliding around on the floor when the patient places his or her foot on it or into the under-coil-opening 13, the IMP device 10 uses several soft rubber-like bottom tabs 17 as shown in FIG. 2.

Figure 3:
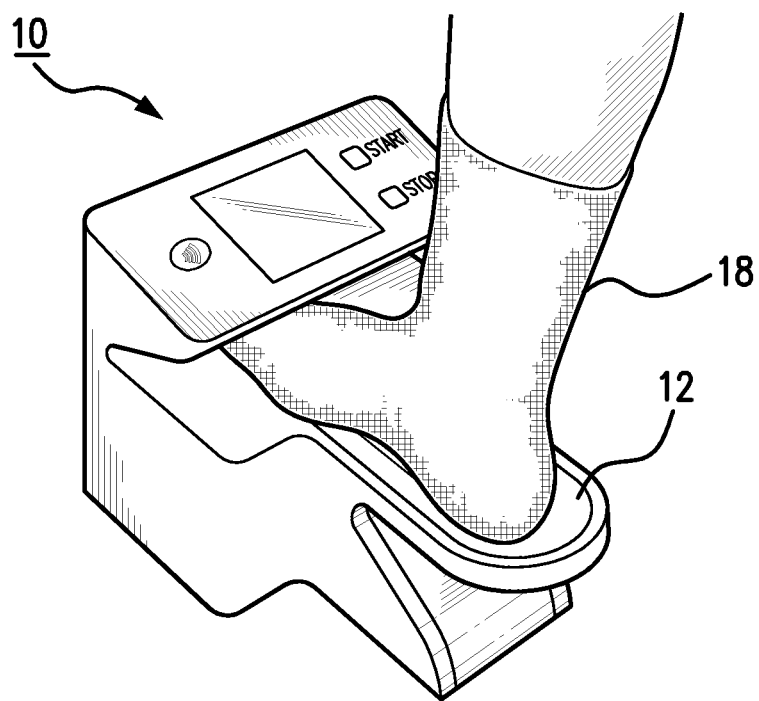
FIG. 3 illustrates a human foot placed upon the top of the magnetic coil of the IMP device.

FIG. 3 illustrates a patient's foot 18 being placed on the top of the coil 12 for the application of a series of intense magnetic pulsations to eliminate or decrease that patient's foot pain. In actual clinical trials, it has been noted that treating only the bottom of a patient's foot (as shown in FIG. 3), has provided most patients with complete relief for that patient's foot pain.

Figure 4:
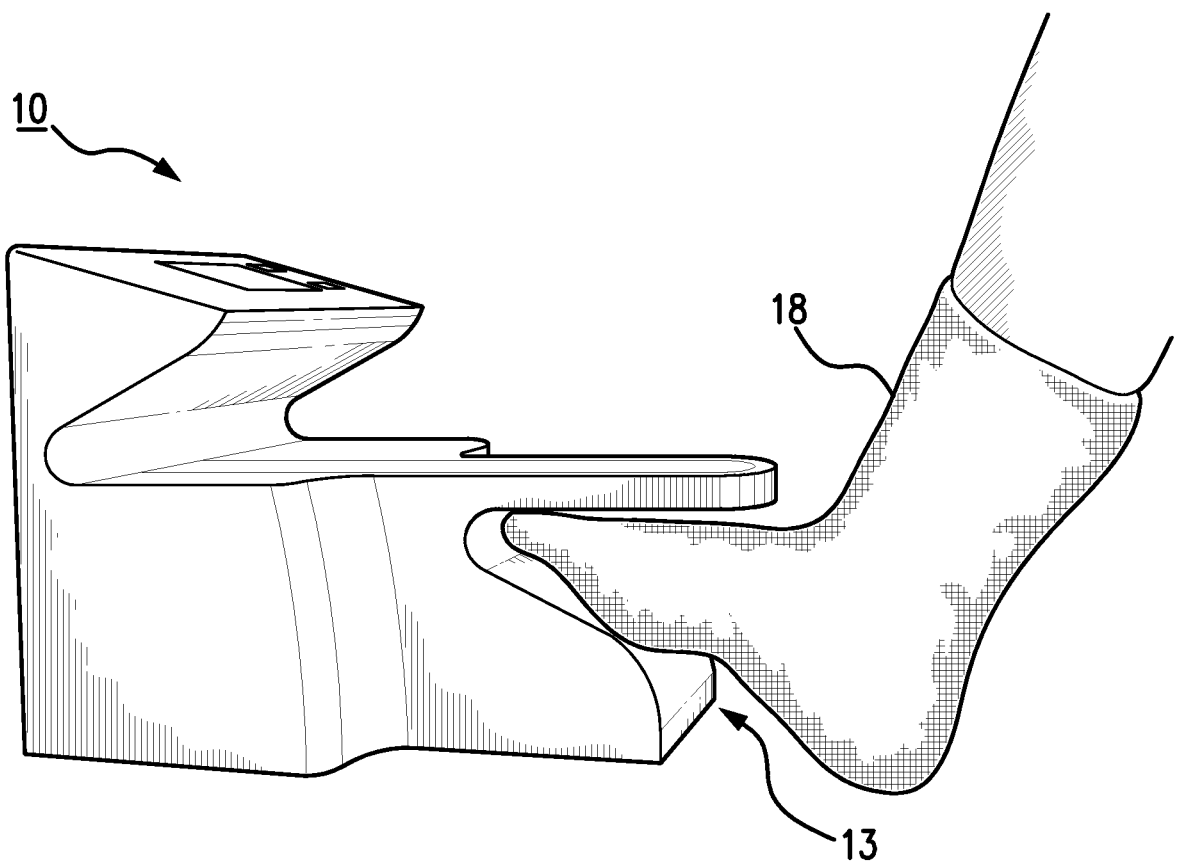
FIG. 4 illustrates a human foot that is placed under the coil of the IMP device to eliminate or decrease pain in the top of that patient's foot.

FIG. 4 illustrates a patient's foot 18 being placed into the under-coil-opening 13 for the treatment of pain on the top of that patient's foot. When treatment as shown in FIG. 3 is not adequate for complete relief of the patient' foot pain, being exposed to a series of magnetic pulsations onto the top of the foot, as shown in FIG. 4, is often successful in achieving a complete relief of that patient's foot pain.

If the patient has back-of-the foot pain or ankle pain, then he/she could place his or her ankle on top of the coil 12 in a variety of positions to gain relief from pain at the back of the foot or in that patient's ankle. For most patients, that will not be needed.

Figure 5:
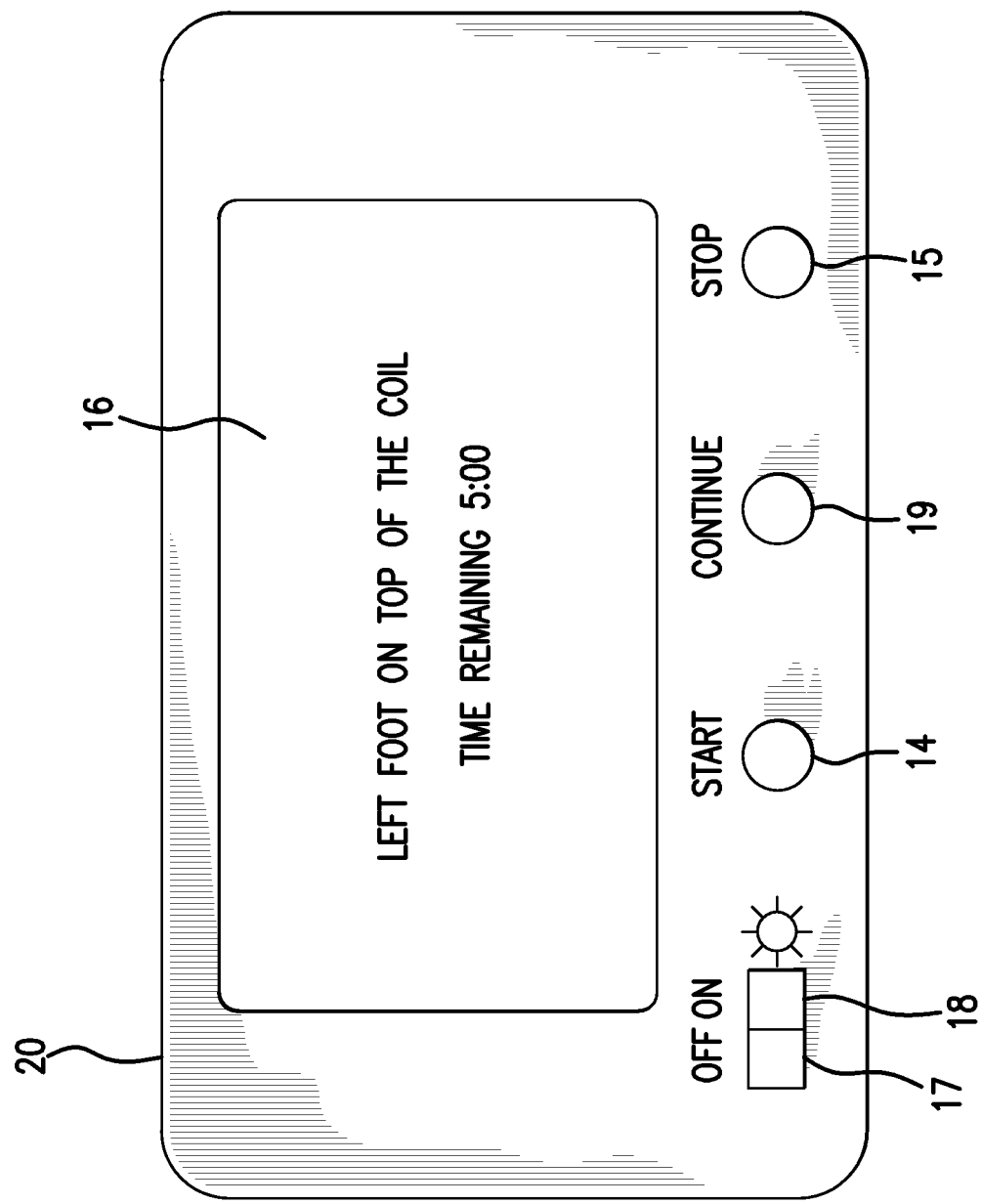
FIG. 5 illustrates the control panel that the patient would see when looking at the top of the IMP device.

FIG. 5 illustrates a more sophisticated control panel 20 as compared to that which is shown in FIGS. 1 and 2. For this control panel 20, there would be an ON-OFF button 17 with the ON-state being indicated by the light 18 going on. The START button 14 and STOP button 15 would have the same functions as described for FIGS. 1 and 2. The CONTINUE button 19 would be used to continue a sequence of magnetic pulsations as is described herein.

Examples of what can be shown on the display panel 16 for different foot pain treatment scenarios are listed below. After a doctor or the patient turns the ON-OFF switch to ON, the first words to appear on the display panel 16 would be:

1. Place Left Foot on Top of the Foot Coil

After a set time period of about 5 to 10 seconds the next statement would be:

2. Press the Start Button

Once the start button is pressed, the patient begins to be exposed to a series of intense magnetic pulsations. The number of magnetic pulses could be from as few as three pulsations to as many as 100 pulsations with an optimum number of pulses being about 50. The strength of each pulse at the surface of the coil 12 would typically be between as little as 0.2 Tesla to as strong as 2.0 Tesla. The rate of pulsations could be as fast as one per second or as slow as one every 30 seconds. In actual practice, one pulse every 6 seconds (that is, 10 pulses per minute) with a peak magnetic pulse intensity of 1.2 Tesla has been found to be highly effective in the treatment of foot pain.

After the start button 14 is pressed, the display 16 will show the time remaining for a treatment in minutes and seconds in the format starting with:

3: Left Foot on Top of the Coil; Time Remaining 5:00

Thirty seconds later it will read 4:30 and so on until it reaches the time 0:10 when it will state:

4. Get Ready to Place Right Foot on Top of the Coil 0:10

At some time to be selected between 0.10 and 0.00, preferably at the time 0:003, the display 16 will say:

5. Place Right Foot on Top the Coil; Time Remaining 0:03

As soon as the time 0:00 is reached, then the next display on the control panel display 16 will be:

6. Right Foot on Top of the Coil; Time Remaining 5:00 and the time will count down to 0:00.

At the time 0:00 the magnetic pulses will stop, and the control panel display 16 will state:

7. Do You Wish to Continue?

If the patient wishes to continue, then he/she or the medical doctor or the nurse helping the patient will press the CONTINUE button 19 on the face of the control panel 20. If the CONTINUE button 19 is not pressed within 5 to 10 seconds the display 16 will state:

8. Treatment Completed

If the CONTINUE button is pressed, then the next wording to appear on the display panel 16 will be:

9. Place Left Foot Under the Coil

Then 5 seconds later the display 16 will state:

10. Press Start

Then there will be a repeat of the wording used when the patient's foot was placed on the top of the coil 12. So that the next display on the display 16 will be:

11. Left Foot Under the Coil; Time Remaining 5:00

Then the time will go down from 5:00 to 0:10 at which time the display 16 will show:

12. Get Ready to Place Right Foot Under the Coil: 0:10 at the time 0:03 the display 16 will state:

13. Right Foot Under the Coil; Time Remaining 5:00 when the countdown reaches 0:00, the display 16 will show:

14. Treatment Completed

At which time the power to the coil will cease.

If at any time, any patient would feel some discomfort or actual pain in his/her foot or ankle, then the STOP button 15 could be pushed to stop the magnetic pulsations. More likely, if there would be an urgent reason to stop like an important phone call or other event, then, in that case, the STOP button 15 could be pressed and that would result in a cessation of the magnetic pulses from the coil 12. If that event occurs, the patient would resume his/her treatment from the start.

For very few of the foot pain patients, it will be desirable to place their ankle and/or the back of their foot on top of the coil 12 for a treatment. If that would be the case, then the patient's physician, or a specially trained nurse to visit the patient at home would be used to show the patient how to do a treatment for the back of the foot or the ankle. That treatment would be accomplished by following the same instructions as were used for the placement of the patient's foot onto the top of the coil, but instead, placing the back of the patient's foot or ankle onto the top of the coil for a treatment would be stated.

If a patient would be unable to bend over to operate the IMP 10, it is conceived that one of the patient's feet could be used by that patient to actuate buttons placed on a top surface of the IMP 10 to control that patient's treatment for his/her foot pain.

Figure 6:
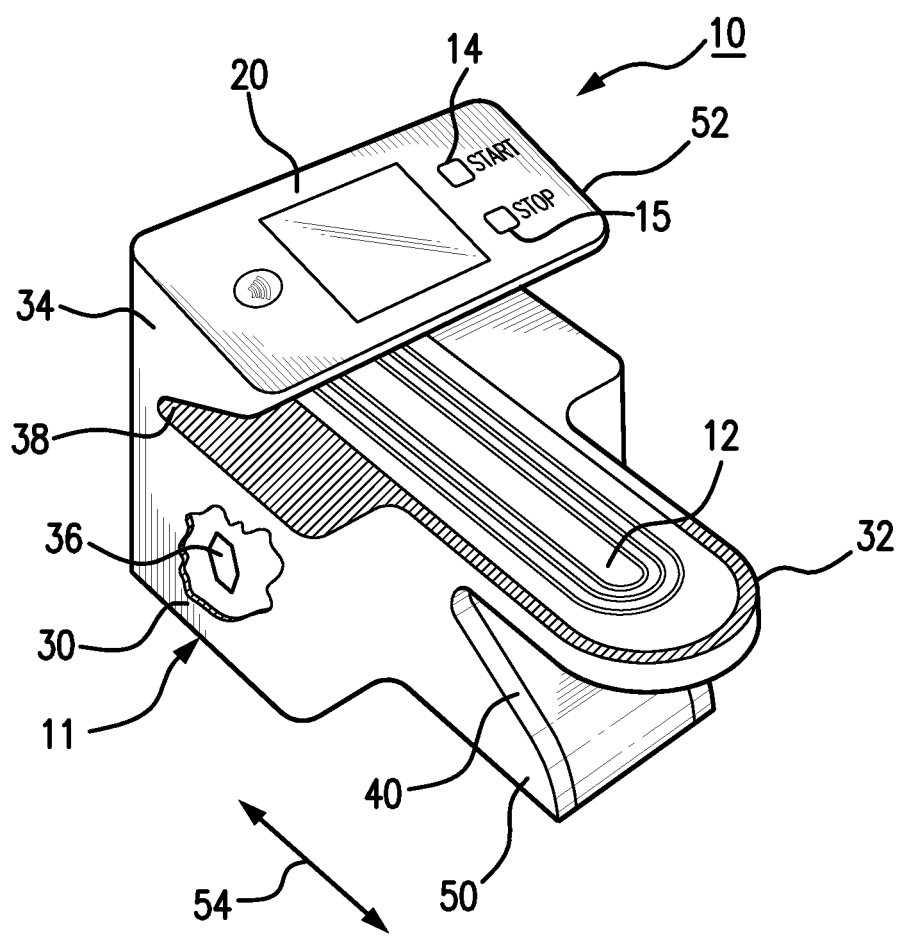
FIG. 6 is a schematic perspective, partially broken away perspective view of the IMP device showing placement of the electrical generator within the IMP device casing; and, FIG. 7 is a schematic side view partially cut away of the IMP device.
Figure 7:
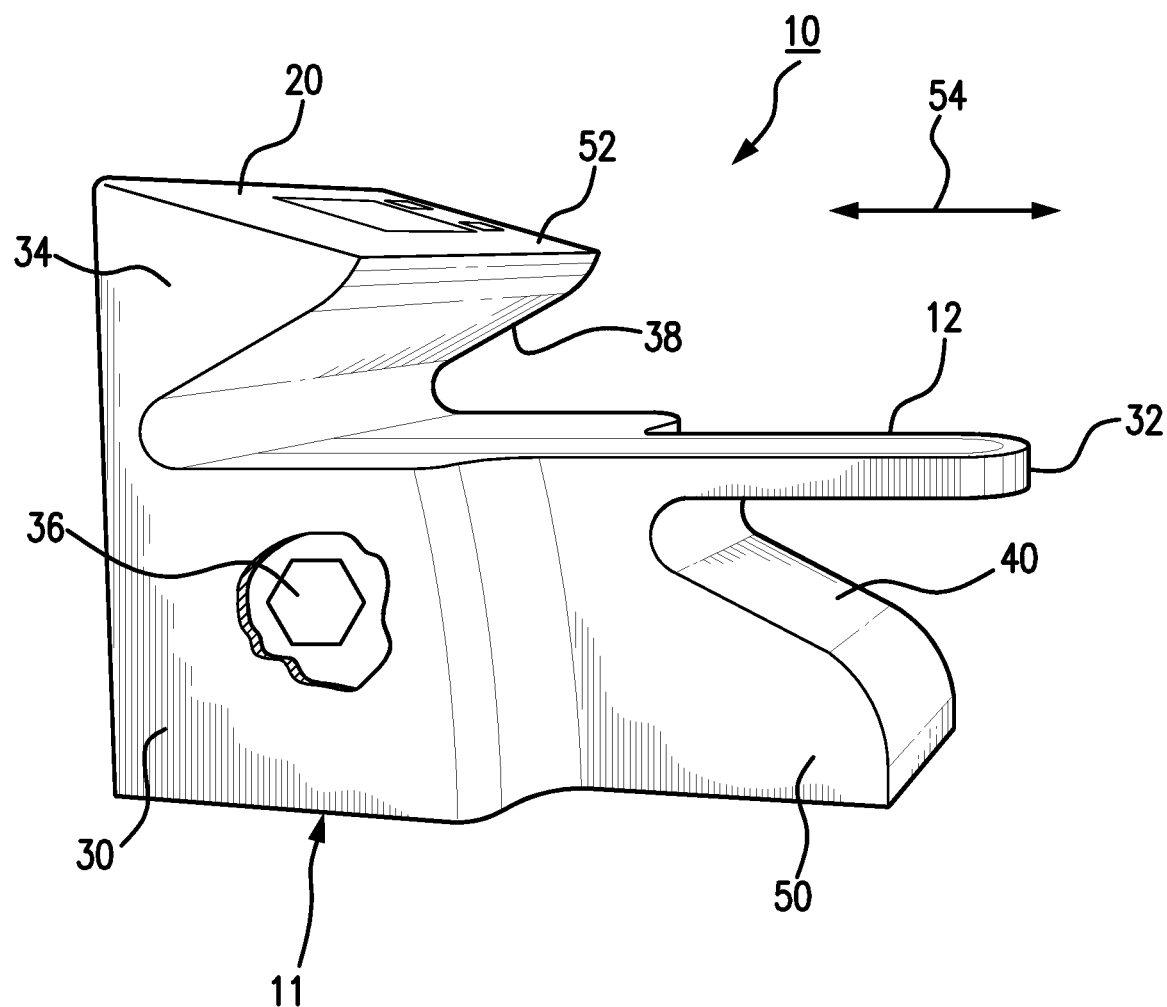

Referring now to FIGS. 6 and 7 there is shown a more detailed explanation of the IMP device construction where it is seen that the IMP device includes a casing 11 having a lower section 30, a casing ledge section 32 for interfacing with portions of the patient's foot, and an upper casing section 34 containing the control panel 20 and associated electronic circuitry.

The casing or housing 11 contains the electrical generator 36 which is positioned in the casing 11, generally in the lower casing section 30. A magnetic coil 12 is coupled to the electrical pulse generator 36 for creating a series of magnetic pulsations. The magnetic coil is is mounted in the casing ledge section 32 and is adapted to be positioned adjacent a bottom of a patient's foot when the patient's foot is inserted into a first recess formed between the casing ledge section 32 and the casing upper section 34.

A second recess or under coil opening 40 is formed between the lower casing section and the casing ledge section 32 which is adapted for insert of the patient's foot to permit placement of at least a portion of a top of the patient's adjacent to the magnetic coil 12.

The casing upper and lower recesses 34 and 30 are ergonomically contoured for ease of insert of the patient's foot and to this end are generally configured have a general "U" shaped configuration. S can be seen in FIGS. 1-7, the lower recess 40 is formed within the casing lower section 30 with a lower surface of ledge section 2 forming one wall of the lower recess 40 and an upper surface of casing lower extension section 50 forming a second wall of the recess 40. As can be seen the casing lower extension upper surface is contoured in a somewhat arcuate manner to allow ease of insert and providing a contour which is comfortable while the treatment session is ongoing. Similarly the upper recess 30 is formed between the casing upper section 34 and the casing ledge section 32, with the upper recess 38 being formed between the casing upper section 34 and the ledge section 32. The casing upper section 34 has an extension 52 of casing upper section 34 which extends in longitudinal direction 54. The casing extension section or portion has a lower surface forming one wall or upper recess 38 with the other surface of the upper recess defined by the ledge 32 upper surface which is generally planar in contour. The lower surface of the extension section 52 is slightly arcuately contoured to accommodate the patient's foot contour, with the upper surface of the ledge section 32 being substantially planar and the ledge section 32 forming a stabilization platform and the means for transmitting the magnetic pulses.

The casing ledge section 32, containing the magnetic coil 12 is substantially planar in configuration extending in the longitudinal direction 54 and provides a stabilization member for the patient's upper foot surface and lower foot surface when the patient's foot is inserted into the lower recess 38 and the upper or second recess 40 or first recess 38.

Although this invention has been described in connection with specific forms and embodiments thereof, it will be appreciated that various modifications other than those discussed above may be resorted to without departing from the spirit or scope of the invention as defined by the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A device for treatment of foot pain by application of a series of intense magnetic pulsations onto a patient's foot, the device comprising:
   an electrical pulse generator and a generally flat magnetic coil each placed within a single enclosure, the electrical pulse generator being capable of creating a series of electrical pulsations having a peak electrical current of at least 100 Amperes which electrical current pulses are placed into the generally flat magnetic coil to create a series of magnetic pulsations that have a maximum magnetic pulse amplitude of at least 0.3 Tesla, the device including a place where the patient's foot can be placed onto a top of the magnetic coil and a second place where the patient's foot can be placed into an opening under the coil to expose the top of the patient's foot to an underside portion of the magnetic coil, the device including a control panel that controls operation of the pulse generator and indicates to the patient how the patient treats himself or herself to ease foot pain.

2. The device of claim 1 wherein the flat magnetic coil is of a substantially oval shape and is wound from a wire with as few as 6 turns of the wire to as many as 20 turns of the wire.

3. The device of claim 2 wherein the cross section of the wire for the magnetic coil has the general shape of a rectangle.

4. The device of claim 1 wherein the device includes a series of bottom tabs so that the device will tend to not be moved when the device is placed on a floor and a patient's foot is placed onto or into the device.

5. The device of claim 1 wherein there is a control panel placed generally at a top of the device, the control panel having an ON-OFF switch to turn the device on or off.

6. The device of claim 5 having a button marked START which, when pressed, begins a series of magnetic pulses to be created by the magnetic coil so that the magnetic pulsations can enter one of the patient's feet.

7. The device of claim 5 having a button marked STOP that can stop creation of any magnetic pulses by the device.

8. The device of claim 5 having a button marked CONTINUE that allows the patient to continue a series of magnetic pulsations onto a top of the patient's foot by having the patient place his/her foot into the opening under the coil of the device.

9. The device of claim 5 wherein a series of instructions are displayed on a display panel of the control panel, the series of instructions informing the patient as to how to carry out a treatment onto his/her feet to decrease or eliminate foot pain suffered by the patient.

10. A method for treatment of foot pain comprising:
    placing a patient's foot onto a magnetic coil that is electrically and mechanically connected to an electrical pulse generator;
    sending a series of magnetic pulses to the patient's foot for relief of said patient's foot pain;
    alternatively placing a second foot of the patient onto the magnetic coil; and
    sending a second series of magnetic pulses to the second foot of the patient for relief of said patient's foot pain;
    wherein the magnetic coil and electric pulse generator are placed on a floor; and
    the patient first places each foot successively onto a top of the magnetic coil for a treatment then successively places each foot into an opening under the coil for treatment of a top of the patient's feet.

11. The method of claim 10 wherein the patient is subjected to at least three magnetic pulsations onto each foot, each pulsation having a strength of at least 0.3 Tesla.

12. The method of claim 11 wherein the patient is subjected to 100+/−75 magnetic pulses that have a peak magnetic field intensity of 1.2+/−0.8 Tesla.

13. The method of claim 10 wherein the patient further places his/her an ankle onto the top of the magnetic coil to undergo a magnetic pulsations treatment for pain in the ankle.

14. A device for treatment of foot pain comprising:
    a casing having a lower section, a ledge section, and an upper section;
    an electrical pulse generator mounted in said casing; and
    a magnetic coil being mounted within said ledge section and adapted to be positioned adjacent a bottom of a patient's foot when said patient's foot is inserted into a first recess formed between said ledge section and said upper section of said casing.

15. The device as recited in claim 14 including an undercoil opening or second recess formed between said lower section and said casing ledge section and adapted for insertion of the patient's foot for placement of a top of the patient's foot adjacent to said magnetic coil.

16. The device as recited in claim 15 where said first and second recesses are ergonomically configured for ease of insertion of the patient's foot.

17. The device as recited in claim 15 where said casing lower section, said casing ledge section, and said casing upper section are formed in one-piece formation.

18. The device as recited in claim 15 where the ledge section of the casing is substantially planar in configuration and extends in a longitudinal direction and is adapted to provide a stabilized platform for an upper foot surface and lower foot surface of said patient when said patient's foot is inserted into said second recess or said first recess respectively.

19. The device as recited in claim 14 including a control panel formed on a top surface of said upper section of said casing for controlling operating parameters of the electrical generator and a set of magnetic pulses.

* * * * *